US009789279B2

(12) United States Patent
Burkholz et al.

(10) Patent No.: US 9,789,279 B2
(45) Date of Patent: Oct. 17, 2017

(54) ANTIMICROBIAL OBTURATOR FOR USE WITH VASCULAR ACCESS DEVICES

(71) Applicant: Becton, Dickinson and Company, Franklin Lakes, NJ (US)

(72) Inventors: Jonathan Karl Burkholz, Salt Lake City, UT (US); Siddarth K. Shevgoor, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 276 days.

(21) Appl. No.: 14/260,071

(22) Filed: Apr. 23, 2014

(65) Prior Publication Data
US 2015/0306345 A1    Oct. 29, 2015

(51) Int. Cl.
| | |
|---|---|
| *A61M 5/32* | (2006.01) |
| *A61M 25/00* | (2006.01) |
| *A61M 25/01* | (2006.01) |
| *A61M 25/06* | (2006.01) |
| *A61M 39/02* | (2006.01) |
| *A61M 39/20* | (2006.01) |

(Continued)

(52) U.S. Cl.
CPC .......... *A61M 25/0043* (2013.01); *A61L 2/00* (2013.01); *A61L 2/26* (2013.01); *A61L 9/00* (2013.01);
(Continued)

(58) Field of Classification Search
CPC ...... A61M 25/0017; A61M 2025/0018; A61M 2025/0019; A61M 39/16; A61M 39/162; A61M 39/165; A61M 39/20; A61M 2039/0285; A61M 2039/0288; A61M 2205/0205; A61M 2025/0056; A61M 25/0111; A61L 2202/24
(Continued)

(56) References Cited

U.S. PATENT DOCUMENTS

| | | |
|---|---|---|
| 3,223,629 A | 12/1965 | Loeffler |
| 3,695,921 A | 10/1972 | Shepherd |
| 3,867,937 A | 2/1975 | Schwartz |
| 3,986,508 A | 10/1976 | Barrington |
| 4,068,660 A | 1/1978 | Beck |
| 4,170,996 A | 10/1979 | Wu |
| 4,280,500 A | 7/1981 | Ono |

(Continued)

FOREIGN PATENT DOCUMENTS

| | | |
|---|---|---|
| CA | 1 331 333 | 8/1994 |
| CA | 2133053 A1 | 3/1995 |

(Continued)

OTHER PUBLICATIONS

McDonnell, G., Russell, A.D. Antiseptics and Disinfectants: Activity, Action, and Resistance. Clinical Microbiology Reviews, (1999) 12(1), pp. 149-179.

(Continued)

*Primary Examiner* — Emily Schmidt
(74) *Attorney, Agent, or Firm* — Jeanne Lukasavage; Craig Metcalf; Kirton McConkie

(57) ABSTRACT

An obturator can include antimicrobial features which assist in sterilizing or maintaining the sterility of fluid contained within a vascular access device while the device is not being used for infusion or other access to the patient's vasculature. These antimicrobial features include antimicrobial coatings applied to various surfaces of an obturator and antimicrobial components bonded or otherwise secured to an obturator. Various combinations of antimicrobial coatings and/or components can be used on an obturator as necessary to provide a desired amount of antimicrobial agents within a particular enclosed volume of a vascular access device.

14 Claims, 9 Drawing Sheets

(51) Int. Cl.
*A61L 2/26* (2006.01)
*A61M 39/16* (2006.01)
*A61M 39/18* (2006.01)
*A61L 29/16* (2006.01)
*A61L 2/00* (2006.01)
*A61L 9/00* (2006.01)

(52) U.S. Cl.
CPC ......... *A61L 29/16* (2013.01); *A61M 25/0102* (2013.01); *A61M 25/0111* (2013.01); *A61M 25/0606* (2013.01); *A61M 39/0247* (2013.01); *A61M 39/16* (2013.01); *A61M 39/18* (2013.01); *A61M 39/20* (2013.01); *A61L 2300/404* (2013.01); *A61M 2025/0018* (2013.01); *A61M 2025/0019* (2013.01); *A61M 2025/0056* (2013.01); *A61M 2039/0285* (2013.01)

(58) Field of Classification Search
USPC ................ 604/262, 264, 265, 523, 533, 539
See application file for complete search history.

(56) References Cited

U.S. PATENT DOCUMENTS

| | | |
|---|---|---|
| 4,334,551 A | 6/1982 | Pfister |
| 4,339,336 A | 7/1982 | Hammond et al. |
| 4,387,879 A | 6/1983 | Tauschinski |
| 4,449,693 A | 5/1984 | Gereg |
| 4,512,766 A | 4/1985 | Vailancourt |
| 4,584,192 A | 4/1986 | Dell et al. |
| 4,592,920 A | 6/1986 | Murtfeldt |
| 4,603,152 A | 7/1986 | Laurin et al. |
| 4,610,674 A | 9/1986 | Suzuki |
| 4,629,743 A | 12/1986 | Hong |
| 4,629,746 A | 12/1986 | Michl et al. |
| 4,642,126 A | 2/1987 | Zador et al. |
| 4,676,782 A | 6/1987 | Yamamoto et al. |
| 4,677,143 A | 6/1987 | Laurin et al. |
| 4,716,032 A | 12/1987 | Westfall et al. |
| 4,723,948 A | 2/1988 | Clark |
| 4,758,225 A | 7/1988 | Cox |
| 4,781,703 A | 11/1988 | Walker |
| 4,798,594 A | 1/1989 | Hillstead |
| 4,838,873 A | 6/1989 | Landskron |
| 4,842,591 A | 6/1989 | Luther |
| 4,846,812 A | 7/1989 | Walker |
| 4,874,377 A | 10/1989 | Newgard |
| 4,880,414 A | 11/1989 | Whipple |
| 4,895,566 A | 1/1990 | Lee |
| 4,897,427 A | 1/1990 | Barnavon et al. |
| 4,915,934 A | 4/1990 | Tomlinson |
| 4,917,668 A | 4/1990 | Haindl |
| 4,925,668 A | 5/1990 | Khan et al. |
| 4,933,178 A | 6/1990 | Capelli |
| 4,935,010 A | 6/1990 | Cox |
| 4,950,257 A | 8/1990 | Hibbs |
| 4,955,890 A | 9/1990 | Yamamoto et al. |
| 4,985,399 A | 1/1991 | Matsuda et al. |
| 4,990,357 A | 2/1991 | Karakelle |
| 5,019,096 A | 5/1991 | Fox, Jr. et al. |
| 5,023,082 A | 6/1991 | Friedman et al. |
| 5,030,665 A | 7/1991 | Lee |
| 5,041,097 A | 8/1991 | Johnson |
| 5,053,014 A | 10/1991 | Van Heugten |
| 5,062,836 A | 11/1991 | Wendell |
| 5,064,416 A | 11/1991 | Newgard |
| 5,077,352 A | 12/1991 | Elton |
| 5,078,703 A | 1/1992 | Bryant |
| 5,084,023 A | 1/1992 | Lemieux |
| 5,085,645 A | 2/1992 | Purdy |
| 5,098,410 A | 3/1992 | Kerby |
| 5,108,374 A | 4/1992 | Lemieux |
| 5,127,905 A | 7/1992 | Lemieux |
| 5,154,703 A | 10/1992 | Bonaldo |
| 5,156,596 A | 10/1992 | Balbierz |
| 5,167,647 A | 12/1992 | Wijkamp |
| 5,217,493 A | 6/1993 | Raad et al. |
| 5,226,898 A | 7/1993 | Gross |
| 5,234,410 A | 8/1993 | Graham |
| 5,242,425 A | 9/1993 | White |
| 5,256,145 A | 10/1993 | Atkinson |
| 5,290,246 A | 3/1994 | Yamamoto |
| 5,295,969 A | 3/1994 | Fischell |
| 5,330,435 A | 7/1994 | Vaillancourt |
| 5,330,449 A | 7/1994 | Prichard |
| 5,350,363 A | 9/1994 | Goode |
| 5,352,205 A | 10/1994 | Dales |
| 5,357,636 A | 10/1994 | Dresdner, Jr. et al. |
| 5,366,505 A | 11/1994 | Farber |
| 5,380,301 A | 1/1995 | Prichard |
| 5,405,323 A | 4/1995 | Rogers |
| 5,405,338 A | 4/1995 | Kranys |
| 5,456,675 A | 10/1995 | Wolbring |
| 5,456,948 A | 10/1995 | Mathisen et al. |
| 5,487,728 A | 1/1996 | Vaillancourt |
| 5,512,199 A | 4/1996 | Khan et al. |
| 5,520,666 A | 5/1996 | Choudhury |
| 5,536,258 A | 7/1996 | Folden |
| 5,540,661 A | 7/1996 | Tomisaka et al. |
| 5,547,662 A | 8/1996 | Khan et al. |
| 5,549,566 A | 8/1996 | Elias |
| 5,549,577 A | 8/1996 | Siegel |
| 5,575,769 A | 11/1996 | Vaillancourt |
| 5,613,663 A | 3/1997 | Schmidt |
| 5,616,338 A | 4/1997 | Fox, Jr. et al. |
| 5,620,434 A | 4/1997 | Brony |
| 5,629,006 A | 5/1997 | Hoang et al. |
| 5,638,812 A | 6/1997 | Turner |
| 5,651,772 A | 7/1997 | Arnett |
| 5,653,695 A | 8/1997 | Hopkins et al. |
| 5,657,963 A | 8/1997 | Hinchliffe |
| 5,658,253 A | 8/1997 | Piontek |
| 5,688,747 A | 11/1997 | Khan |
| 5,697,915 A | 12/1997 | Lynn |
| 5,698,229 A | 12/1997 | Ohsumi et al. |
| 5,712,229 A | 1/1998 | Hopkins et al. |
| 5,716,406 A | 2/1998 | Farber |
| 5,738,144 A | 4/1998 | Rogers |
| 5,749,861 A | 5/1998 | Guala |
| 5,763,412 A | 6/1998 | Khan et al. |
| 5,773,487 A | 6/1998 | Sokol |
| 5,806,831 A | 9/1998 | Paradis |
| 5,810,768 A | 9/1998 | Lopez |
| 5,817,069 A | 10/1998 | Arnett |
| 5,827,239 A | 10/1998 | Dillon |
| 5,830,196 A | 11/1998 | Hicks |
| 5,830,401 A | 11/1998 | Prichard |
| 5,833,674 A | 11/1998 | Turnbull |
| 5,843,046 A | 12/1998 | Motisi |
| 5,861,440 A | 1/1999 | Gohla et al. |
| 5,911,710 A | 6/1999 | Barry |
| 5,951,519 A | 9/1999 | Utterberg |
| 5,954,698 A | 9/1999 | Pike |
| 5,957,898 A | 9/1999 | Jepson |
| 5,967,490 A | 10/1999 | Pike |
| 6,039,302 A | 3/2000 | Cote, Sr. |
| 6,046,143 A | 4/2000 | Khan et al. |
| 6,051,609 A | 4/2000 | Yu et al. |
| 6,068,622 A | 5/2000 | Sater |
| 6,074,379 A | 6/2000 | Prichard |
| 6,077,244 A | 6/2000 | Botich |
| 6,102,890 A | 8/2000 | Stivland |
| 6,117,108 A | 9/2000 | Woehr |
| 6,120,784 A | 9/2000 | Snyder, Jr. |
| 6,127,320 A | 10/2000 | van Ooij et al. |
| 6,156,054 A | 12/2000 | Zadno-Azizi |
| 6,165,168 A | 12/2000 | Russo |
| 6,171,287 B1 | 1/2001 | Lynn |
| 6,217,566 B1 | 4/2001 | Ju |
| 6,228,073 B1 | 5/2001 | Noone |
| 6,242,526 B1 | 6/2001 | Siddiqui et al. |
| 6,245,098 B1 | 6/2001 | Feeser |

(56) References Cited

U.S. PATENT DOCUMENTS

| | | |
|---|---|---|
| 6,248,811 B1 | 6/2001 | Ottersbach et al. |
| 6,273,404 B1 | 8/2001 | Holman |
| 6,273,869 B1 | 8/2001 | Vaillancourt |
| 6,326,417 B1 | 12/2001 | Jia |
| 6,332,874 B1 | 12/2001 | Eliasen |
| 6,337,357 B1 | 1/2002 | Fukunishi et al. |
| 6,344,218 B1 | 2/2002 | Dodd et al. |
| 6,353,041 B1 | 3/2002 | Qian |
| 6,387,075 B1 | 5/2002 | Stivland |
| 6,413,539 B1 | 7/2002 | Shalaby |
| 6,426,373 B1 | 7/2002 | Stange |
| 6,475,434 B1 | 11/2002 | Darouiche |
| 6,485,473 B1 | 11/2002 | Lynn |
| 6,488,942 B1 | 12/2002 | Ingemann |
| 6,492,445 B2 | 12/2002 | Siddiqui et al. |
| 6,503,353 B1 | 1/2003 | Peterson |
| 6,511,462 B1 | 1/2003 | Itou |
| 6,544,214 B1 | 4/2003 | Utterberg |
| 6,575,958 B1 | 6/2003 | Happ |
| 6,575,960 B2 | 6/2003 | Becker |
| 6,576,633 B1 | 6/2003 | Young et al. |
| 6,579,221 B1 | 6/2003 | Peterson |
| 6,579,539 B2 | 6/2003 | Lawson et al. |
| 6,595,981 B2 | 7/2003 | Huet |
| 6,663,614 B1 | 12/2003 | Carter |
| 6,699,221 B2 | 3/2004 | Vaillancourt |
| 6,719,726 B2 | 4/2004 | Meng |
| 6,719,991 B2 | 4/2004 | Darouiche et al. |
| 6,723,350 B2 | 4/2004 | Burrell et al. |
| 6,740,063 B2 | 5/2004 | Lynn |
| 6,808,161 B1 | 10/2004 | Hishikawa |
| 6,843,784 B2 | 1/2005 | Modak et al. |
| 6,846,846 B2 | 1/2005 | Modak et al. |
| 6,861,060 B1 | 3/2005 | Luriya et al. |
| 6,883,778 B1 | 4/2005 | Newton |
| 6,887,270 B2 | 5/2005 | Miller et al. |
| 6,893,456 B2 | 5/2005 | Lumauig |
| 6,896,889 B2 | 5/2005 | Chevalier et al. |
| 7,008,404 B2 | 3/2006 | Nakajima |
| 7,074,839 B2 | 7/2006 | Fansler et al. |
| 7,098,256 B2 | 8/2006 | Ong et al. |
| 7,115,183 B2 | 10/2006 | Larson |
| 7,179,849 B2 | 2/2007 | Terry |
| 7,198,800 B1 | 4/2007 | Ko |
| 7,232,428 B1 | 6/2007 | Inukai |
| 7,232,540 B2 | 6/2007 | Gould et al. |
| 7,261,925 B2 | 8/2007 | Nesbitt |
| 7,268,165 B2 | 9/2007 | Greten et al. |
| 7,347,839 B2 | 3/2008 | Hiejima |
| 7,374,798 B2 | 5/2008 | Choo et al. |
| 7,396,346 B2 | 7/2008 | Nakajima |
| 7,407,707 B2 | 8/2008 | Gould et al. |
| 7,462,401 B2 | 12/2008 | Halfyard et al. |
| 7,470,254 B2 | 12/2008 | Basta |
| 7,494,339 B2 | 2/2009 | Dias et al. |
| 7,498,367 B2 | 3/2009 | Qian |
| 7,514,477 B2 | 4/2009 | Klare et al. |
| 7,608,082 B2 | 10/2009 | Cuevas |
| 7,704,935 B1 | 4/2010 | Davis et al. |
| 7,736,339 B2 | 6/2010 | Woehr |
| 7,816,434 B2 | 10/2010 | Hackbarth et al. |
| 7,871,649 B2 | 1/2011 | Modak et al. |
| 7,874,467 B2 | 1/2011 | Pardes |
| 7,914,494 B2 | 3/2011 | Hiejima |
| 7,981,475 B2 | 7/2011 | Takahashi |
| 8,034,454 B2 | 10/2011 | Terry |
| 8,034,455 B2 | 10/2011 | Wang et al. |
| 8,067,402 B2 | 11/2011 | Whiteford et al. |
| 8,133,423 B2 | 3/2012 | Tang |
| 8,227,050 B1 | 7/2012 | O'Neil |
| 8,231,602 B2 | 7/2012 | Anderson |
| 8,263,102 B2 | 9/2012 | Labrecque et al. |
| 8,268,381 B2 | 9/2012 | Whiteford et al. |
| 8,343,523 B2 | 1/2013 | Toreki et al. |
| 8,343,525 B2 | 1/2013 | Davis et al. |
| 8,353,876 B2 | 1/2013 | Suwito |
| 8,357,119 B2 | 1/2013 | Stout |
| 8,388,583 B2 | 3/2013 | Stout et al. |
| 8,414,547 B2 | 4/2013 | DiFiore et al. |
| 8,512,294 B2 | 8/2013 | Ou-Yang et al. |
| 8,622,995 B2 | 1/2014 | Ziebol et al. |
| 8,622,996 B2 | 1/2014 | Ziebol et al. |
| 8,691,887 B2 | 4/2014 | Ou-Yang |
| 8,728,030 B2 | 5/2014 | Woehr |
| 8,840,927 B2 | 9/2014 | Ditizio |
| 9,078,441 B2 | 7/2015 | Raad |
| 9,138,252 B2 | 9/2015 | Bierman |
| 2001/0010016 A1 | 7/2001 | Modak et al. |
| 2001/0016589 A1 | 8/2001 | Modak et al. |
| 2001/0018095 A1 | 8/2001 | Shlenker |
| 2001/0032006 A1 | 10/2001 | Griffin, III et al. |
| 2001/0049519 A1 | 12/2001 | Holman |
| 2001/0053895 A1 | 12/2001 | Vaillancourt |
| 2001/0056133 A1 | 12/2001 | Montgomery et al. |
| 2002/0009436 A1 | 1/2002 | Doyle et al. |
| 2002/0022660 A1 | 2/2002 | Jampani et al. |
| 2002/0028751 A1 | 3/2002 | Lokkesmoe et al. |
| 2002/0037260 A1 | 3/2002 | Budny et al. |
| 2002/0040092 A1 | 4/2002 | Siddiqui et al. |
| 2002/0064858 A1 | 5/2002 | Yacoby-Zeevi |
| 2002/0091424 A1 | 7/2002 | Biel |
| 2002/0119111 A1 | 8/2002 | Kilgour et al. |
| 2002/0133124 A1 | 9/2002 | Leinsing et al. |
| 2002/0144705 A1 | 10/2002 | Brattesani et al. |
| 2003/0023208 A1 | 1/2003 | Osypka |
| 2003/0060804 A1 | 3/2003 | Vaillancourt |
| 2003/0068667 A1 | 4/2003 | Olson |
| 2003/0072781 A1 | 4/2003 | Pelerin |
| 2003/0105143 A1 | 6/2003 | Ammendola et al. |
| 2003/0119932 A1 | 6/2003 | Al-Akhdar et al. |
| 2003/0134783 A1 | 7/2003 | Harshey et al. |
| 2003/0144362 A1 | 7/2003 | Utterberg |
| 2003/0147932 A1 | 8/2003 | Nun et al. |
| 2003/0162839 A1 | 8/2003 | Symington et al. |
| 2003/0170308 A1 | 9/2003 | Cleary et al. |
| 2003/0176848 A1 | 9/2003 | Gibson et al. |
| 2003/0206875 A1 | 11/2003 | Budny et al. |
| 2003/0215433 A1 | 11/2003 | Kokai-Kun et al. |
| 2003/0224032 A1 | 12/2003 | Read et al. |
| 2004/0013574 A1 | 1/2004 | Conway |
| 2004/0013703 A1 | 1/2004 | Ralph |
| 2004/0014864 A1 | 1/2004 | Milic et al. |
| 2004/0039349 A1 | 2/2004 | Modak et al. |
| 2004/0058829 A1 | 3/2004 | Hei et al. |
| 2004/0062592 A1 | 4/2004 | Shekalim |
| 2004/0109852 A1 | 6/2004 | Xu |
| 2004/0115477 A1 | 6/2004 | Nesbitt |
| 2004/0132164 A1 | 7/2004 | Doyle et al. |
| 2004/0180829 A1 | 9/2004 | Bassler et al. |
| 2004/0185296 A1 | 9/2004 | Mazzanti |
| 2004/0230162 A1 | 11/2004 | Tan |
| 2004/0234475 A1 | 11/2004 | Lannibois-Drean et al. |
| 2005/0008671 A1 | 1/2005 | Van Antwerp |
| 2005/0048005 A1 | 3/2005 | Stockel |
| 2005/0048124 A1 | 3/2005 | Sarangapani |
| 2005/0059731 A1 | 3/2005 | Albrecht et al. |
| 2005/0080158 A1 | 4/2005 | Ong et al. |
| 2005/0100580 A1 | 5/2005 | Osborne et al. |
| 2005/0118239 A1 | 6/2005 | Sabesan |
| 2005/0124970 A1 | 6/2005 | Kunin |
| 2005/0131356 A1 | 6/2005 | Ash et al. |
| 2005/0143286 A1 | 6/2005 | Singh et al. |
| 2005/0148928 A1 | 7/2005 | Molina |
| 2005/0158253 A1 | 7/2005 | Budny et al. |
| 2005/0176905 A1 | 8/2005 | Moon et al. |
| 2005/0209581 A1 | 9/2005 | Butts |
| 2005/0209583 A1 | 9/2005 | Powers |
| 2005/0233950 A1 | 10/2005 | Madhyastha |
| 2005/0265931 A1 | 12/2005 | Qian |
| 2006/0024372 A1 | 2/2006 | Utterberg |
| 2006/0051385 A1 | 3/2006 | Scholz |
| 2006/0064159 A1 | 3/2006 | Porter |
| 2006/0163515 A1 | 7/2006 | Ruschke |
| 2006/0165751 A1 | 7/2006 | Chudzik |

(56) References Cited

U.S. PATENT DOCUMENTS

| | | |
|---|---|---|
| 2006/0165903 A1 | 7/2006 | Mazzanti |
| 2006/0177477 A1 | 8/2006 | Ash |
| 2006/0239954 A1 | 10/2006 | Sancho |
| 2006/0258780 A1 | 11/2006 | Chaussade et al. |
| 2006/0259012 A1 | 11/2006 | Propp |
| 2006/0281663 A1 | 12/2006 | Asmus |
| 2007/0000407 A1 | 1/2007 | Leong |
| 2007/0083157 A1 | 4/2007 | Belley |
| 2007/0083162 A1 | 4/2007 | O'Reagan |
| 2007/0112112 A1 | 5/2007 | Kerschner et al. |
| 2007/0112146 A1 | 5/2007 | Falk et al. |
| 2007/0129690 A1 | 6/2007 | Rosenblatt |
| 2007/0141524 A1 | 6/2007 | Brennan et al. |
| 2007/0160547 A1 | 7/2007 | Duffy et al. |
| 2007/0166344 A1 | 7/2007 | Qu et al. |
| 2007/0202177 A1 | 8/2007 | Hoang |
| 2007/0203574 A1 | 8/2007 | McGrath et al. |
| 2007/0225179 A1 | 9/2007 | Schutz et al. |
| 2007/0233007 A1 | 10/2007 | Adams |
| 2007/0275101 A1 | 11/2007 | Lu et al. |
| 2007/0281198 A1 | 12/2007 | Lousenberg |
| 2008/0026026 A1 | 1/2008 | Lu et al. |
| 2008/0027410 A1 | 1/2008 | Harding |
| 2008/0039796 A1 | 2/2008 | Nakajima |
| 2008/0051737 A1 | 2/2008 | Paul et al. |
| 2008/0075761 A1 | 3/2008 | Modak et al. |
| 2008/0103487 A1 | 5/2008 | Miyasaka |
| 2008/0108944 A1 | 5/2008 | Woehr |
| 2008/0119789 A1 | 5/2008 | Kaemmerer |
| 2008/0161763 A1* | 7/2008 | Harding ............... A61M 39/045 604/265 |
| 2008/0182921 A1 | 7/2008 | Suh et al. |
| 2008/0194707 A1 | 8/2008 | Potter |
| 2009/0012220 A1 | 1/2009 | Yamane et al. |
| 2009/0036768 A1 | 2/2009 | Seehusen et al. |
| 2009/0062766 A1 | 3/2009 | Howlett |
| 2009/0101152 A1 | 4/2009 | Burk et al. |
| 2009/0110844 A1 | 4/2009 | Platzer et al. |
| 2009/0114327 A1 | 5/2009 | Breunig |
| 2009/0117164 A1 | 5/2009 | Toreki et al. |
| 2009/0125118 A1 | 5/2009 | Gong |
| 2009/0157007 A1 | 6/2009 | McKinnon |
| 2009/0162530 A1 | 6/2009 | Nesbitt |
| 2009/0176907 A1 | 7/2009 | Subramanian et al. |
| 2009/0188559 A1 | 7/2009 | Nesbitt |
| 2009/0220739 A1 | 9/2009 | Chougule |
| 2009/0226541 A1 | 9/2009 | Scholz et al. |
| 2009/0281525 A1 | 11/2009 | Harding |
| 2009/0317435 A1 | 12/2009 | Vandesteeg et al. |
| 2009/0324666 A1 | 12/2009 | Krongauz et al. |
| 2010/0015200 A1 | 1/2010 | McClain |
| 2010/0024648 A1 | 2/2010 | Breault |
| 2010/0069854 A1 | 3/2010 | Okoh |
| 2010/0106102 A1 | 4/2010 | Ziebol |
| 2010/0106103 A1* | 4/2010 | Ziebol .................. A61L 2/186 604/265 |
| 2010/0135949 A1 | 6/2010 | Ou-Yang |
| 2010/0136209 A1 | 6/2010 | Ou-Yang et al. |
| 2010/0137379 A1 | 6/2010 | Ou-Yang |
| 2010/0137472 A1 | 6/2010 | Ou-Yang |
| 2010/0200017 A1 | 8/2010 | Kerr |
| 2010/0204648 A1 | 8/2010 | Stout et al. |
| 2010/0204675 A1 | 8/2010 | Woehr |
| 2010/0222746 A1 | 9/2010 | Burkholz |
| 2011/0009831 A1 | 1/2011 | Burkholz et al. |
| 2011/0065798 A1 | 3/2011 | Hoang et al. |
| 2011/0146680 A1 | 6/2011 | Conway |
| 2011/0150958 A1 | 6/2011 | Davis et al. |
| 2011/0160663 A1 | 6/2011 | Stout et al. |
| 2011/0218529 A1 | 9/2011 | Garcia |
| 2011/0301553 A1 | 12/2011 | Goral et al. |
| 2011/0319825 A1 | 12/2011 | Goral et al. |
| 2012/0078203 A1 | 3/2012 | Gaube |
| 2012/0083750 A1 | 4/2012 | Sansoucy |
| 2012/0103448 A1 | 5/2012 | Hopf |
| 2013/0090607 A1 | 4/2013 | McKinnon |
| 2013/0165868 A1 | 6/2013 | Isaacson |
| 2013/0196079 A1 | 8/2013 | Schwalm |
| 2013/0245568 A1 | 9/2013 | Kerr |
| 2013/0274686 A1* | 10/2013 | Ziebol ............... A61M 25/0017 604/265 |
| 2013/0310764 A1* | 11/2013 | Burkholz .......... A61M 25/0045 604/246 |
| 2016/0008517 A1 | 1/2016 | Burkholz |

FOREIGN PATENT DOCUMENTS

| | | |
|---|---|---|
| CN | 1187598 C | 2/2003 |
| CN | 1526771 A | 9/2004 |
| CN | 101353545 A | 1/2009 |
| CN | 102070983 A | 5/2011 |
| DE | 4011867 A1 | 10/1991 |
| DE | 202009009602 U1 | 12/2009 |
| EP | 0 036 294 A2 | 9/1981 |
| EP | 0070087 B1 | 1/1983 |
| EP | 0227230 A1 | 7/1987 |
| EP | 0 338 418 A1 | 10/1989 |
| EP | 0370997 A2 | 5/1990 |
| EP | 0379271 B1 | 7/1990 |
| EP | 0 396 431 A2 | 11/1990 |
| EP | 0 414 997 A1 | 3/1991 |
| EP | 0778337 A2 | 6/1997 |
| EP | 0992252 B1 | 4/2000 |
| EP | 1466645 B1 | 10/2004 |
| EP | 1679043 B1 | 7/2006 |
| JP | 05-277434 | 10/1993 |
| JP | 07-051651 | 2/1995 |
| JP | H07-47435 A | 2/1995 |
| JP | 08-209064 | 8/1996 |
| JP | H08-311373 A | 11/1996 |
| JP | 09-151262 | 6/1997 |
| JP | 09-157548 | 6/1997 |
| JP | H09-176677 A | 7/1997 |
| JP | H10-231 A | 1/1998 |
| JP | H11-322560 A | 11/1999 |
| JP | 2000-178475 A | 6/2000 |
| JP | 2000-264803 A | 9/2000 |
| JP | 2001-072438 A | 3/2001 |
| JP | 2002-282762 | 10/2002 |
| JP | 2003-342402 | 12/2003 |
| JP | 2004-043669 A | 2/2004 |
| JP | 2005-028209 A | 2/2005 |
| JP | 2005-515838 A | 6/2005 |
| JP | 2005-520912 A | 7/2005 |
| JP | 2007-016096 A | 1/2007 |
| JP | 2008-533051 A | 8/2008 |
| JP | 2010-536836 A | 12/2010 |
| JP | 2012-532681 A | 12/2012 |
| KR | 20020066429 A | 8/2002 |
| KR | 20080039460 A | 5/2008 |
| WO | 9422522 A1 | 10/1994 |
| WO | 9521648 A1 | 8/1995 |
| WO | 9616690 A1 | 6/1996 |
| WO | 9640359 A1 | 12/1996 |
| WO | 98/58690 | 12/1998 |
| WO | 98/58989 | 12/1998 |
| WO | 9916498 A1 | 4/1999 |
| WO | 99/32168 | 7/1999 |
| WO | 9934849 A1 | 7/1999 |
| WO | 9936490 A1 | 7/1999 |
| WO | 9943971 A1 | 9/1999 |
| WO | 00/66189 | 11/2000 |
| WO | 0074743 A1 | 12/2000 |
| WO | 0195862 A1 | 12/2001 |
| WO | 2004071568 A1 | 8/2004 |
| WO | 2004/108091 A2 | 12/2004 |
| WO | 2005037340 A2 | 4/2005 |
| WO | 2006012446 A2 | 2/2006 |
| WO | 2006056482 A1 | 6/2006 |
| WO | 2006074666 A2 | 7/2006 |
| WO | 2006/088288 A1 | 8/2006 |
| WO | 2006/099358 A2 | 9/2006 |
| WO | 2006099359 A2 | 9/2006 |
| WO | 2006100442 A1 | 9/2006 |

(56) References Cited

FOREIGN PATENT DOCUMENTS

| WO | 2007/064835 A2 | 6/2007 |
| WO | 2007095576 A2 | 8/2007 |
| WO | 2007/100653 A2 | 9/2007 |
| WO | 2007/100776 A2 | 9/2007 |
| WO | 2008/014438 A2 | 1/2008 |
| WO | 2008/014447 A2 | 1/2008 |
| WO | 2008/031601 A1 | 3/2008 |
| WO | 2008/045761 A2 | 4/2008 |
| WO | 2008052790 A2 | 5/2008 |
| WO | 2008/128896 A2 | 10/2008 |
| WO | 2008/132045 A2 | 11/2008 |
| WO | 2008132045 A2 | 11/2008 |
| WO | 2009012336 A1 | 1/2009 |
| WO | 2009/070227 A1 | 6/2009 |
| WO | 2009114833 A1 | 9/2009 |
| WO | 2010093791 A1 | 8/2010 |
| WO | 2011005951 A2 | 1/2011 |
| WO | 2011/034675 A2 | 3/2011 |
| WO | 2011048204 A2 | 4/2011 |
| WO | 2012/036916 A1 | 3/2012 |
| WO | 2013009998 A2 | 1/2013 |
| WO | 2011118680 A1 | 7/2013 |
| WO | 2013134421 A1 | 9/2013 |

OTHER PUBLICATIONS

"ComfortCoat Hydrophilic Coating," DSM in Medical, http://www.dsm.com/en_US/medical/public/home/pages/product-coating-comfortcoat.jsp, Updated Jan. 11, 2013, Printed Apr. 22, 2013.

"Lubricent—Lubricious Hydrophillic Coatings for Medical Devices," Harland Medical Systems, http://www.harlandmedical.com/index.php/materials/lubricent.html, pp. 1-2, Printed Apr. 22, 2013.

"UV & EB Cure," Xiper Innovations, Inc., http://xiperinnovations.com/uv_eb_cure, Printed Apr. 22, 2013.

Cabot Corporation, "Using Silicas and Aluminas in Coatings,", www.cabot-corp.com/Silicas-And-Aluminas/Coatings, downloaded from the Internet on Apr. 26, 2011.

Gama Healthcare, Clinell Alcoholic 2% Chlorhexidine, http://www.gamahealthcare.com/clinellaca2c.html, pp. 1-3, Nov. 7, 2008.

Sage Products, Inc., Preoperative Skin Preparation for the Surgical Patient, http://www.sageproducts.com/products/skin-prep.cfm, 1 page, Oct. 31, 2008.

Sage Products, Inc., Address Multi-Drug Resistant Organisms on the Skin with Early Preop Prep, http://www.sageproducts.com/products/ssi-prevention.cfm, 1 page, Oct. 31, 2008.

Sage Products, Inc., Preoperative Skin Preparation and Perioperative Oral Care for the Short-Term Ventilated Patient, http://www.sageproducts.com/products/ssi-vap-prevention.cfm, 1 page, Oct. 31, 2008.

Enturia, ChloraPrep, http://www.enturia.com/products/chloraPrep/chloraPrep-product.html, pp. 1-3, Oct. 31, 2008.

Anusavice KJ, Zhang N-Z, Shen C. Controlled Release of Chlorhexidine from UDMA-TEGDMA Resin, Journal of dental research, 2006;85(10); 950-954.

Ciba Irgacure 500 data sheet from Ciba Specialty Chamicals, online, retrieved on [Dec. 13, 2015]. Retrieved from internet URL www.conquimica.com/wp-content/uploads/2015/06/ft_irgacure_500.pdf.

Elson Silva, PhD, "Respecting Hydrology Science in the Patenting System," pp. 1-7, Jan. 13, 2011.

* cited by examiner

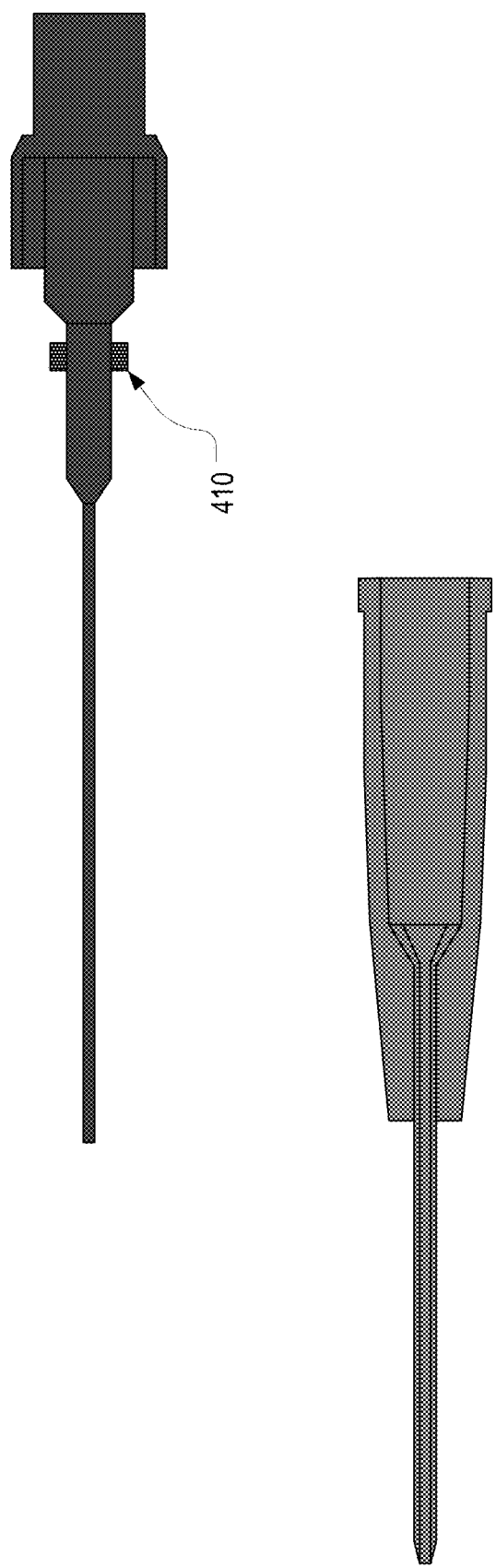

ANTIMICROBIAL OBTURATOR FOR USE WITH VASCULAR ACCESS DEVICES

BACKGROUND OF THE INVENTION

The present invention relates generally to obturators for peripheral IV catheters or other vascular access devices. In particular, the present invention relates to obturators that are configured to provide antimicrobial protection to vascular access devices when the obturators are inserted within the vascular access devices.

Catheters are commonly used for a variety of infusion therapies. For example, catheters are used for infusing fluids, such as normal saline solution, various medicaments, and total parenteral nutrition into a patient, withdrawing blood from a patient, as well as monitoring various parameters of the patient's vascular system.

Catheter-related bloodstream infections are caused by the colonization of microorganisms in patients with intravascular catheters and I.V. access devices. These infections are an important cause of illness and excess medical costs. More importantly, these infections often result in patient deaths.

Many techniques have been employed to reduce the risk of infection from a catheter or other intravenous device. For example, catheters have been designed that employ an antimicrobial lubricant or an antimicrobial coating on an inner or outer surface of the catheter. Similarly, antimicrobial lubricants or coatings have been applied to the surfaces of other components of a catheter assembly, components attached to the catheter assembly, or other medical devices which may come in direct contact with the patient's vasculature or in contact with a fluid that may enter the patient's vasculature. Further, some devices or components are made of a material that is impregnated with an antimicrobial agent.

Although these techniques have been beneficial, there are various drawbacks that limit their usefulness. For example, it can be difficult and/or expensive to apply an antimicrobial coating or lubricant to the complex internal and external geometries of many devices or components. Also, some devices or components are preferably made of a material that is not suitable for the application of an antimicrobial coating or that cannot be impregnated with an antimicrobial agent. Because of such difficulties, the current techniques for providing antimicrobial protection are oftentimes not used or, if used, are not adequately applied to provide maximum antimicrobial protection.

BRIEF SUMMARY OF THE INVENTION

The present invention extends to obturators for vascular access devices. An obturator configured in accordance with the present invention can include antimicrobial features which assist in sterilizing or maintaining the sterility of fluid contained within a vascular access device while the device is not being used for infusion or other access to the patient's vasculature.

These antimicrobial features include antimicrobial coatings applied to various surfaces of an obturator and antimicrobial components bonded or otherwise secured to an obturator. Various combinations of antimicrobial coatings and/or components can be used on an obturator as necessary to provide a desired amount of antimicrobial agents within a particular enclosed volume of a vascular access device.

In one embodiment, the present invention is implemented as an obturator for a vascular access device. The obturator includes a catheter portion configured to be inserted through a lumen of the vascular access device and into a proximal end of a catheter of the vascular access device while the catheter is placed intravenously within a patient, and a cap portion configured to secure the obturator to the vascular access device. The catheter portion includes an antimicrobial coating configured to release an antimicrobial agent into fluid contained within the vascular access device.

In another embodiment, the present invention is implemented as an obturator for a vascular access device. The obturator includes a catheter portion configured to be inserted through a lumen of the vascular access device and into a proximal end of a catheter of the vascular access device while the catheter is placed intravenously within a patient, a middle portion configured to be positioned within the lumen of the vascular access device while the catheter portion is inserted into the catheter, and a cap portion configured to secure the obturator to the vascular access device. The obturator further includes an antimicrobial ring positioned around the middle portion. The antimicrobial ring is configured to release an antimicrobial agent into fluid contained within the lumen of the vascular access device.

In another embodiment, the present invention is implemented as an obturator for a vascular access device. The obturator includes a catheter portion configured to be inserted through a lumen of the vascular access device and into a proximal end of a catheter of the vascular access device while the catheter is placed intravenously within a patient, and a base portion configured to be inserted into the lumen to seal the lumen. The obturator further includes an antimicrobial component that is configured to release an antimicrobial agent into fluid contained within the lumen of the vascular access device.

This summary is provided to introduce a selection of concepts in a simplified form that are further described below in the Detailed Description. This Summary is not intended to identify key features or essential features of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 1A illustrates a perspective front view of the obturator prior to being inserted into a vascular access device. FIG. 1B illustrates a cross-sectional front view of the obturator of FIG. 1A prior to being inserted into a vascular access device. FIG. 1C illustrates the obturator of FIGS. 1A and 1B after the obturator has been inserted into a vascular access device which in this example is a peripheral intravenous catheter.

FIG. 2A illustrates a perspective front view of the obturator prior to being inserted into a vascular access device. FIG. 2B illustrates a cross-sectional front view of the obturator of FIG. 2A prior to being inserted into a vascular access device. FIG. 2C illustrates the obturator of FIGS. 2A and 2B after the obturator has been inserted into a vascular access device which in this example is a peripheral intravenous catheter. FIG. 2D illustrates a cut-away perspective front view of the obturator of FIGS. 2A-2C when the obturator is positioned within a ported catheter.

FIG. 3A illustrates the obturator prior to being inserted into the vascular access device. FIG. 3B illustrates the obturator after being inserted into the vascular access device as well as how an antimicrobial agent contained within the antimicrobial agent is released into fluid contained within the lumen of the vascular access device.

FIGS. 4A and 4B provide cross-sectional front views of an obturator having an antimicrobial ring and a vascular access device. FIG. 4A illustrates the obturator prior to being inserted into the vascular access device. FIG. 4B illustrates the obturator after being inserted into the vascular access device as well as how an antimicrobial agent contained within the antimicrobial ring is released into fluid contained within the lumen of the vascular access device.

DETAILED DESCRIPTION OF THE INVENTION

Figure 1A:
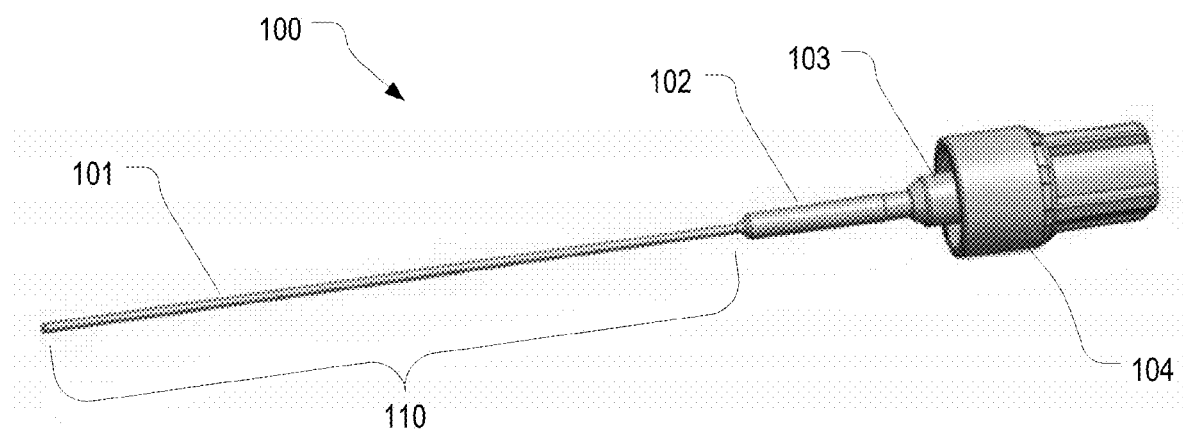
FIGS. 1A-1C each illustrate an obturator that includes an antimicrobial coating in accordance with one or more embodiments of the invention.

The present invention extends to obturators for vascular access devices. An obturator configured in accordance with the present invention can include antimicrobial features which assist in sterilizing or maintaining the sterility of fluid contained within a vascular access device while the device is not being used for infusion or other access to the patient's vasculature.

These antimicrobial features include antimicrobial coatings applied to various surfaces of an obturator and antimicrobial components bonded or otherwise secured to an obturator. Various combinations of antimicrobial coatings and/or components can be used on an obturator as necessary to provide a desired amount of antimicrobial agents within a particular enclosed volume of a vascular access device.

In one embodiment, the present invention is implemented as an obturator for a vascular access device. The obturator includes a catheter portion configured to be inserted through a lumen of the vascular access device and into a proximal end of a catheter of the vascular access device while the catheter is placed intravenously within a patient, and a cap portion configured to secure the obturator to the vascular access device. The catheter portion includes an antimicrobial coating configured to release an antimicrobial agent into fluid contained within the vascular access device.

In another embodiment, the present invention is implemented as an obturator for a vascular access device. The obturator includes a catheter portion configured to be inserted through a lumen of the vascular access device and into a proximal end of a catheter of the vascular access device while the catheter is placed intravenously within a patient, a middle portion configured to be positioned within the lumen of the vascular access device while the catheter portion is inserted into the catheter, and a cap portion configured to secure the obturator to the vascular access device. The obturator further includes an antimicrobial ring positioned around the middle portion. The antimicrobial ring is configured to release an antimicrobial agent into fluid contained within the lumen of the vascular access device.

In another embodiment, the present invention is implemented as an obturator for a vascular access device. The obturator includes a catheter portion configured to be inserted through a lumen of the vascular access device and into a proximal end of a catheter of the vascular access device while the catheter is placed intravenously within a patient, and a base portion configured to be inserted into the lumen to seal the lumen. The obturator further includes an antimicrobial component that is configured to release an antimicrobial agent into fluid contained within the lumen of the vascular access device.

An obturator for a vascular access device is commonly used as a means of sealing the lumen of a catheter of a vascular access device while the catheter is positioned intravenously but is not being used for infusion, medication administration, or other types of vascular access. As an example, an obturator may be inserted within a peripheral intravenous catheter when the peripheral intravenous catheter will not be used to access the patient's vasculature for a substantial amount of time (e.g. 24 hours).

Figure 1B:
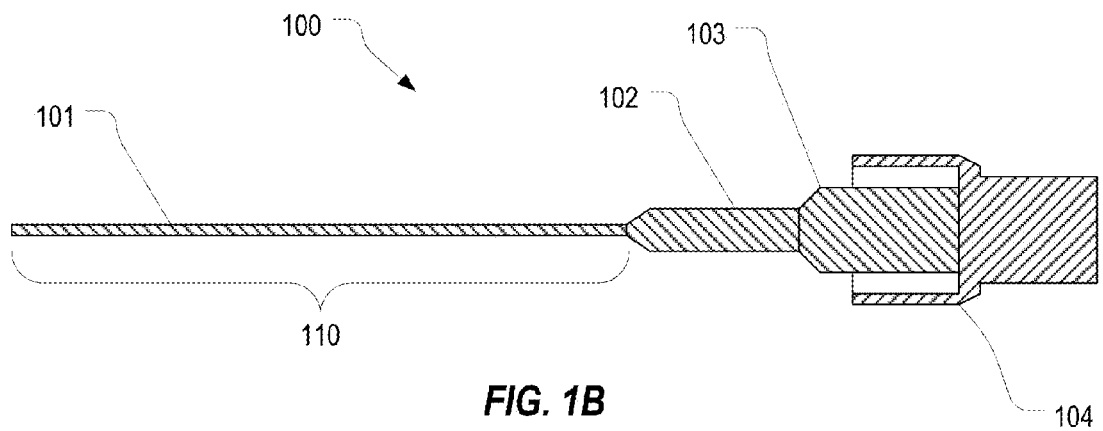
Figure 1C:
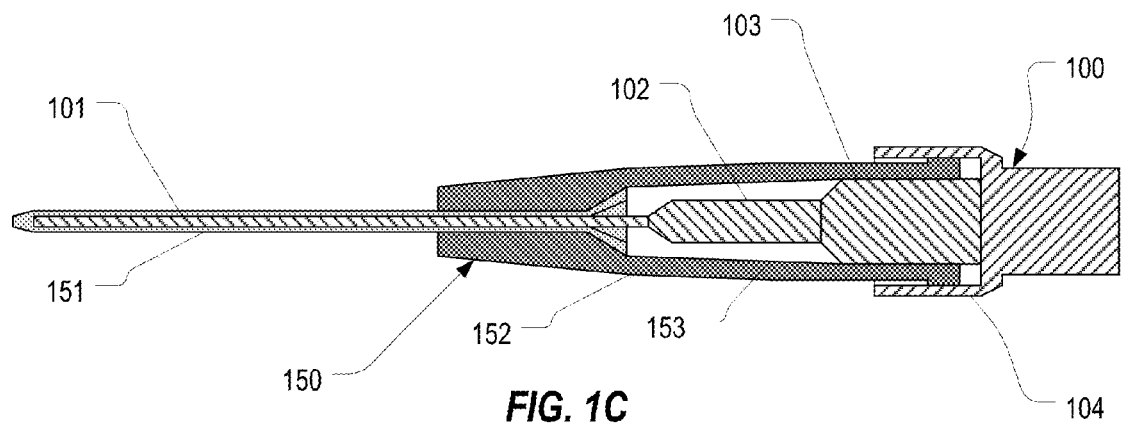

FIGS. 1A-1C illustrate an example embodiment of an obturator configured in accordance with the present invention. FIG. 1A illustrates a perspective view of an obturator 100 that is configured to be inserted within a peripheral intravenous catheter or another vascular access device, FIG. 1B illustrates a cross-sectional view of obturator 100, and FIG. 1C illustrates a cross-sectional view of obturator 100 when inserted into a peripheral intravenous catheter 150.

Obturator 100 includes a catheter portion 101, a middle portion 102, a base portion 103, and a cap portion 104. Catheter portion 101 is sized so that is can be inserted within the catheter of a peripheral intravenous catheter. In many cases, the outer diameter of catheter portion 101 is configured to be substantially the same as the inner diameter of the catheter of a peripheral intravenous catheter in which obturator 100 is to be used so that catheter portion 101 forms a seal preventing the flow of fluids through the catheter. Accordingly, catheter portion 101 can be defined as the portion of the obturator that is configured to be inserted into a catheter of a vascular access device.

Catheter portion 101 can be configured with various lengths. For example, the length of catheter portion 101 can be configured so that the distal end of catheter portion 101 is positioned at or near the distal end of the catheter. Alternatively, the length of catheter portion 101 can be configured so that the distal end of catheter portion 101 extends distally out from the catheter. Similarly, the length of catheter portion 101 can be configured so that the distal end of the catheter portion is positioned proximally to the distal end of the catheter. In short, the specific length of catheter portion 101 is not essential to the invention and any length of catheter portion 101 can be employed as long as catheter portion 101 extends at least partially into the catheter when obturator 100 is inserted into the vascular access device.

Middle portion 102 comprises a length of obturator 100 that is positioned between catheter portion 101 and base portion 103. In FIGS. 1A-1C, middle portion 102 is shown as having a larger diameter than catheter portion 101. However, middle portion 102 could also be configured with a diameter that is the same as or less than the diameter of catheter portion 101. Middle portion 102 is positioned between catheter portion 101 and base portion 103 so that it remains within the lumen of the vascular access device in which obturator 100 is placed. Accordingly, middle portion 102 refers more particularly to a length of the obturator rather than to a separate or distinguishable portion of the obturator. Therefore, even though the figures identify middle portion 102 as a length of the obturator having a different diameter than the other portions, this is not required.

Base portion 103 comprises a portion of obturator 100 having a diameter that is substantially the same as the diameter of the lumen of the vascular access device in which the obturator is used. Therefore, a purpose of base portion 103 is to seal the lumen of a vascular access device. Although the figures illustrate obturators that include base portions configured to seal the lumen of a vascular access device, an obturator in accordance with the present invention does not require a base portion configured in this manner. For example, an obturator can include a base portion that has a diameter that is less than the diameter of the lumen such that the base portion does not seal the lumen.

Cap portion 104 comprises a proximal portion of obturator 100 that is configured to secure the obturator to the vascular access device. In some embodiments such as is shown in the figures, cap portion 104 can be configured to extend overtop the proximal end of the vascular access device. In such embodiments, an inner surface of cap portion 104 can include threads for locking the cap portion 104 to the vascular access device. Alternatively, an inner surface of cap portion 104 can be configured to form a friction fit with the outer surface of the vascular access device. In other embodiments, cap portion 104 can be designed so that no portion extends overtop the exterior of the vascular access device. In essence, a cap portion 104 can be defined as the portion of the obturator that the user grips to insert and remove the obturator from a vascular access device. In many cases, cap portion 104 will also form a cover overtop the proximal opening of the vascular access device, but this is not required by the invention.

Although this description describes an obturator as including distinct catheter, middle, base, and cap portions, the intent of this description is to assist in the understanding of the invention and should not be construed as limiting the claims. In particular, an obturator in accordance with the present invention could be configured only with distinct cap and catheter portions with the cap portion being the portion that a user grips and the catheter portion extending distally from the cap portion.

In accordance with one or more embodiments of the invention, obturator 100 can also include an antimicrobial coating on one or more portions. The location of the antimicrobial coating can be selected so that the antimicrobial coating will be in contact with residual fluid that remains within the vascular access device after use. As this residual fluid contacts the antimicrobial coating, one or more antimicrobial agents contained within the coating can be dispersed (e.g. eluted or dissolved) into the residual fluid thereby sterilizing or maintaining the sterility of the fluid. In this way, the risk of microbial colonization within the vascular access device is reduced.

As depicted in FIGS. 1A-1C, an antimicrobial coating 110 (which is not visible in these figures) can be applied to catheter portion 101. Antimicrobial coating 110 can extend along any length of catheter portion 110. As depicted in these figures, antimicrobial coating extends from a distal tip of catheter portion 101 to middle portion 102. In some embodiments, antimicrobial coating 110 could also extend along middle portion 102 and/or base portion 103. In other embodiments, antimicrobial coating 110 may only be applied on middle portion 102 and/or base portion 103.

As shown in FIG. 1C, obturator 100 can be inserted into a peripheral intravenous catheter 150 (or another vascular access device). Peripheral intravenous catheter 150 comprises a catheter adapter 152 having a lumen 153, and a catheter 151 that extends distally from catheter adapter 152. As shown, obturator 100 can be inserted into peripheral intravenous catheter 150 so that catheter portion 101 extends into catheter 151. Cap portion 104 can be configured to extend overtop the proximal end/opening of catheter adapter 152.

In the example shown in FIG. 1C, base portion 103 is configured with a diameter that is substantially the same as the diameter of lumen 153. Therefore, when obturator 100 is fully inserted into peripheral intravenous catheter 150, base portion 103 forms a seal within lumen 153. Also, with obturator 100 fully inserted, the proximal end of catheter portion 101 is positioned within lumen 153. As such, a portion of catheter portion 101 that includes antimicrobial coating 110 is contained within lumen 153. In this way, any residual fluid within lumen 153 can come in contact with antimicrobial coating 110 which enables the antimicrobial agents contained within antimicrobial coating to be dispensed within the fluid. Similarly, any fluid that remains within catheter 151 will be in contact with antimicrobial coating 110 on the length of catheter portion 101 that is positioned within catheter 151. Therefore, the antimicrobial agents can be dispensed from obturator 100 both within catheter 151 and lumen 153.

Figure 2A:
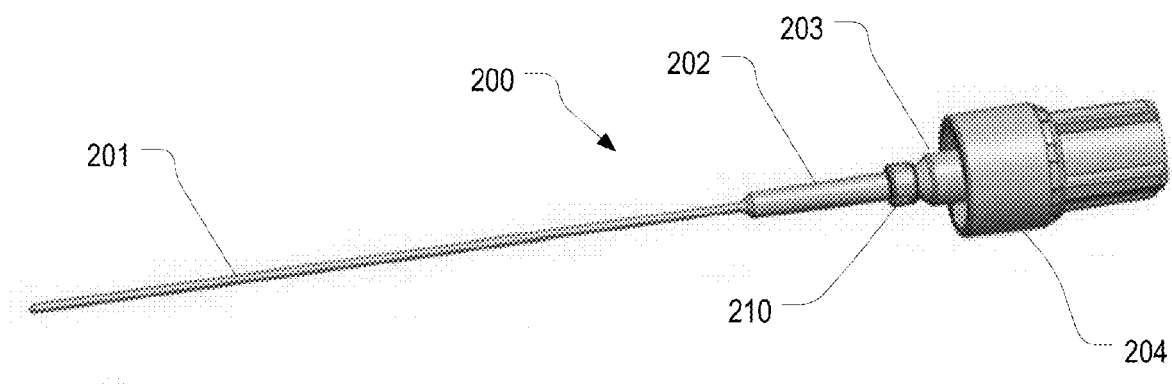
FIGS. 2A-2D each illustrate an obturator that includes an antimicrobial ring in accordance with one or more embodiments of the invention.
Figure 2B:
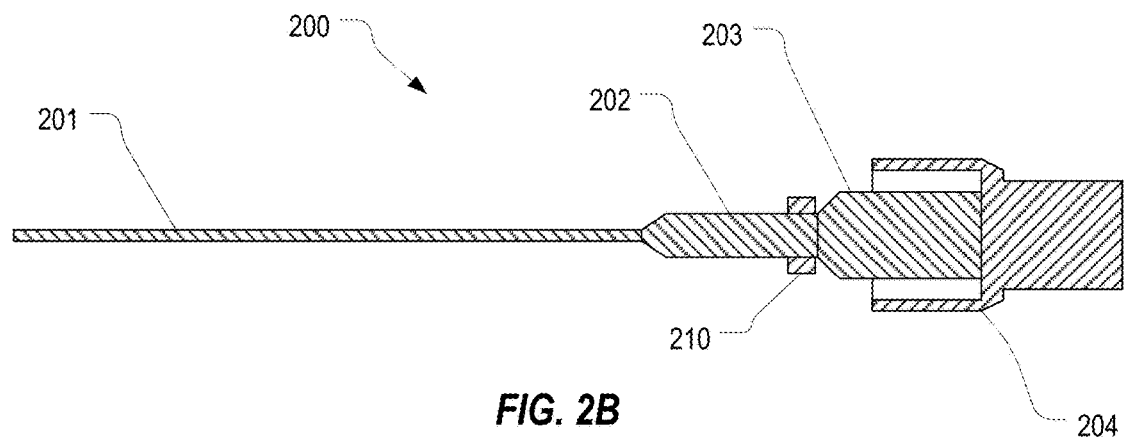
Figure 2C:
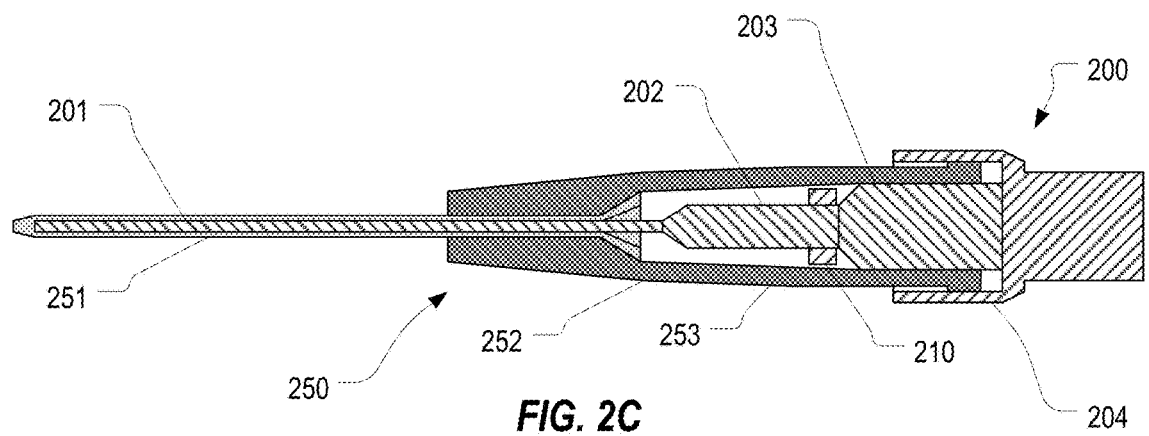
Figure 2D:
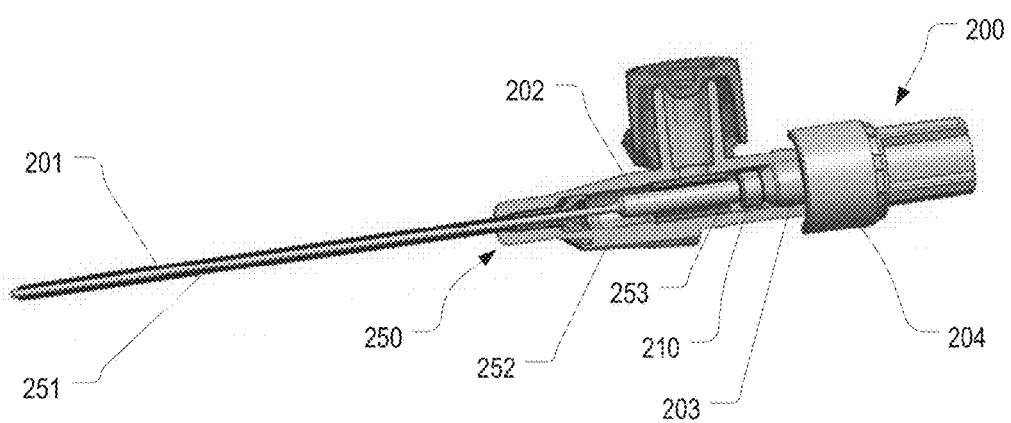

FIGS. 2A-2C illustrate another example embodiment of an obturator configured in accordance with the present invention. FIG. 2A illustrates a perspective view of an obturator 200 that is configured to be inserted within a peripheral intravenous catheter or another vascular access device, FIG. 2B illustrates a cross-sectional view of obturator 200, and FIG. 2C illustrates a cross-sectional view of obturator 200 when inserted into a peripheral intravenous catheter 250.

Obturator 200, like obturator 100, includes a catheter portion 201, a middle portion 202, a base portion 203, and a cap portion 204. In some embodiments, obturator 200 may also include antimicrobial coating 110, as described above, on catheter portion 201. However, in describing FIGS. 2A-2C, it will be assumed that obturator 200 does not include antimicrobial coating 110.

In accordance with one or more embodiments of the invention, obturator 200 can also include an antimicrobial ring 210. Antimicrobial ring 210 can comprise a material that contains one or more antimicrobial agents. As will be further described below, the antimicrobial agents can be contained within the material or on the surface (e.g. as a coating) of the material from which the ring is made. The location of antimicrobial ring 210 can be selected so that the antimicrobial ring will be in contact with residual fluid that remains within the vascular access device after use. As this residual fluid contacts the antimicrobial ring, one or more antimicrobial agents contained within the ring can be dispersed (e.g. eluted or dissolved) into the residual fluid thereby sterilizing or maintaining the sterility of the fluid. In this way, the risk of microbial colonization within the vascular access device is reduced.

As shown in FIGS. 2A-2C, antimicrobial ring 210 is positioned around middle portion 202. Therefore, antimicrobial ring 210 will be positioned within lumen 253 when obturator 200 is inserted into peripheral intravenous catheter 250 as is shown in FIG. 2C. Because antimicrobial ring 210 is positioned within lumen 253, any residual fluid contained in lumen 253 can come in contact with antimicrobial ring 210 thereby causing the antimicrobial agents contained in or on antimicrobial ring 210 to be dispersed into the fluid.

As stated above, in some embodiments, antimicrobial ring 210 can be used on an obturator that also includes an antimicrobial coating 110 on its catheter portion. Using both can ensure that adequate amounts of antimicrobial agents are dispensed in both the catheter and lumen of the catheter adapter since antimicrobial ring 210 can account for the increased amount of antimicrobial agents required to effectively treat the larger volume of the lumen.

In addition to a ring, antimicrobial components of other shapes can also be employed. For example, many differently shaped antimicrobial components can be affixed to an obturator at various locations to provide antimicrobial benefits to a vascular access device. Accordingly, an obturator in accordance with the present invention may include one or more antimicrobial components that are affixed or otherwise secured to the obturator.

Various types of antimicrobial coatings can be employed on obturators in accordance with embodiments of the present invention. In some embodiments, an alcohol-based formulation containing one or more antimicrobial agents can be applied to the surface (e.g. catheter portion 101) of the obturator such as by dipping or spraying. Once applied, the alcohol can dissolve from the surface leaving behind a residue containing the antimicrobial agents thereby forming the antimicrobial coating. In such embodiments, the antimicrobial coating thus formed will dissolve into the fluid within the vascular access device. Using a dissolvable antimicrobial coating can be preferred in many applications where an obturator will be used over a relatively shorter duration of time since the rapid dissolving of the coating results in a quick release of the antimicrobial agents into the fluid. Examples of suitable formulations and methods that can be used to apply the formulations on an obturator are disclosed in U.S. patent application Ser. No. 13/438,559, titled Systems and Methods for Applying a Novel Antimicrobial Coating Material to a Medical Device which is incorporated by reference.

In other embodiments, an antimicrobial coating can be formed of a matrix that includes one or more antimicrobial agents. For example, the matrix can be a polymer or other suitable material that is cured (e.g. via UV curing) or otherwise bonded to the surface of the obturator. In such coatings, the antimicrobial agent will be eluted from the matrix coating in a controlled fashion. Examples of suitable matrixes and methods of applying the matrixes that can be employed to form an antimicrobial coating on an obturator are described in U.S. Pat. No. 8,512,294, titled Vascular Access Device Antimicrobial Materials and Solutions; and U.S. patent application Ser. No. 12/397,760, titled Antimicrobial Compositions; Ser. No. 12/476,997, titled Antimicrobial Coating Compositions; Ser. No. 12/490,235, titled Systems and Methods for Applying an Antimicrobial Coating to a Medical Device; and Ser. No. 12/831,880, titled Antimicrobial Coating for Dermally Invasive Devices; each of which is incorporated by reference.

In some embodiments, an antimicrobial component (e.g. a ring) can be formed of any suitable material and can have an antimicrobial coating formed of either an alcohol-based formulation or a base material matrix and antimicrobial agents as described in the previous paragraphs. In other embodiments, the material from which the antimicrobial component is made can comprise the base material matrix and the antimicrobial agents. In other words, an antimicrobial component can be comprised entirely of a base material matrix or can only have a coating comprised of either the base material matrix or the alcohol-based formulation. In either case, an antimicrobial component can be bonded or mechanically connected to an obturator.

In embodiments of the invention, an obturator can be configured with one or more of the three general types of antimicrobial protection described above. In other words, an obturator can include an antimicrobial coating formed using an alcohol-based formulation, an antimicrobial coating formed of a base material matrix, and an antimicrobial component (whether formed entirely of a base material matrix, having only a coating of a base material matrix, or having a coating of an alcohol-based formulation). Various combinations of these types of antimicrobial protection can be employed on an obturator to give the obturator the desired antimicrobial properties when used within a vascular access device.

In many obturator designs, the catheter portion and base portion of the obturator form seals at opposite ends of the vascular access device effectively creating a locked volume of fluid within the vascular access device. Based on a typical volume of fluid that can be expected to exist within a vascular access device, an obturator can be configured with an appropriate antimicrobial coating and/or component to ensure that the typical volume of fluid will be adequately treated.

To provide an appropriate amount of antimicrobial agents, various factors can be considered including the total surface area or amount (e.g. in weight) of the antimicrobial coating on the obturator, the concentration of the antimicrobial agents within the coating or material, the rate at which the coating or material will elute or dispense the antimicrobial agents, and the type of antimicrobial agent. For example, to achieve a typical inhibitory concentration of 20 ppm for *pseudomonas aeruginosa* in a locked volume of 0.16 cc of fluid within a catheter adapter over a 24 hour period, 3.2 µg of chlorhexidine would need to be released from the obturator. Additionally, to attain a typical bacteriocidal concentration of 500 ppm for *pseudomonas aeruginosa*, a minimum of 80 µg of chlorhexidine would need to be released from the obturator. Accordingly, in an embodiment where the obturator includes an antimicrobial coating formed using an alcohol-based formulation (i.e. a coating from which the agents dissolve) and the obturator is desired to provide protection against *pseudomonas aeruginosa*, an antimicrobial coating having a minimum target weight may range from 3.5 to 81 µg (depending on whether an inhibitory or bacteriocidal concentration is desired). On the other hand, in an embodiment where the obturator includes an antimicrobial coating or component comprised of a base material matrix containing antimicrobial agents (i.e. a coating or component that elutes the agents) and it is desired that the obturator provide antimicrobial protection for a 24 hour period, an antimicrobial coating or component having a surface area as small as 2.5 mm$^2$ may be suitable.

The above examples illustrate that the specific weight of a dissolving antimicrobial coating or surface area of an eluting antimicrobial coating/component can be selected based on the targeted microorganism, the desired antimicrobial effect (e.g. inhibitory or bacteriocidal concentration), the desired duration for which the antimicrobial agents will be effective, the release kinetics (e.g. rate of dissolution or elution) of the coating/component, and the type of antimicrobial agent used (e.g. chlorhexidine gluconate and chlorhexidine diacetate).

One benefit of employing an obturator to distribute antimicrobial agents within a vascular access device between uses of the device is that the obturator can be modified to include an antimicrobial coating and/or component without modifying how the obturator is used. The obturator is therefore a simple means for placing antimicrobial agents in the precise location within the device and at the precise time when they are needed. Another benefit is that an obturator can be provided with an antimicrobial coating and/or component that is configured to distribute a precise amount of antimicrobial agent to the internal volume of the device. As described above, the coating and/or component can be customized based on various factors to provide the necessary amount of antimicrobial agents for a given volume and for a desired purpose.

Figure 3A:
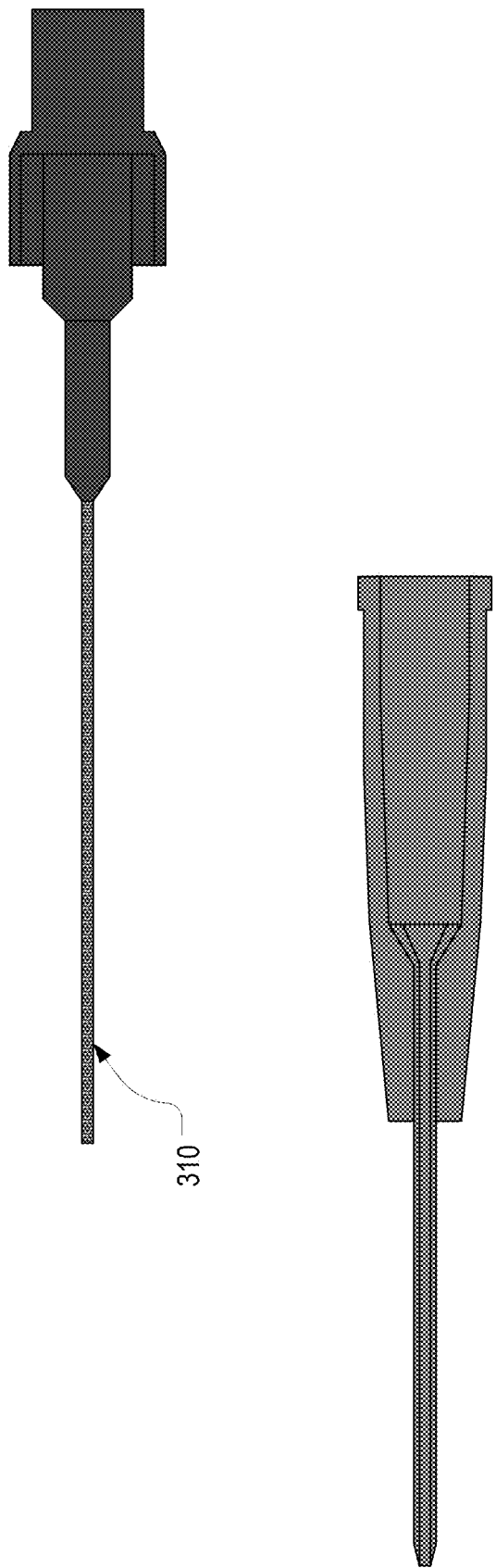
FIGS. 3A and 3B provide cross-sectional front views of an obturator having an antimicrobial coating and a vascular access device.
Figure 3B:
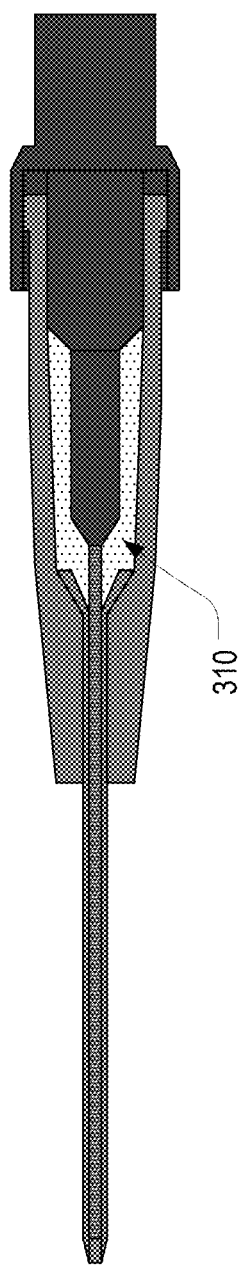

FIGS. 3A and 3B provide an example of how an antimicrobial coating 310 on an obturator can disperse antimicrobial agents into fluid contained within a vascular access device. In these figures, the antimicrobial coating is represented using the white dots shown on the catheter portion of the obturator. FIG. 3B illustrates that when the obturator is placed within the vascular access device, antimicrobial agents are dispersed into the fluid which is represented by the black dots being dispersed throughout the lumen of the device. In this example, it is assumed that the lumen is full of fluid. However, the antimicrobial agent can be dispersed to fluid within the lumen even when the fluid does not fill the lumen.

Figure 4B:
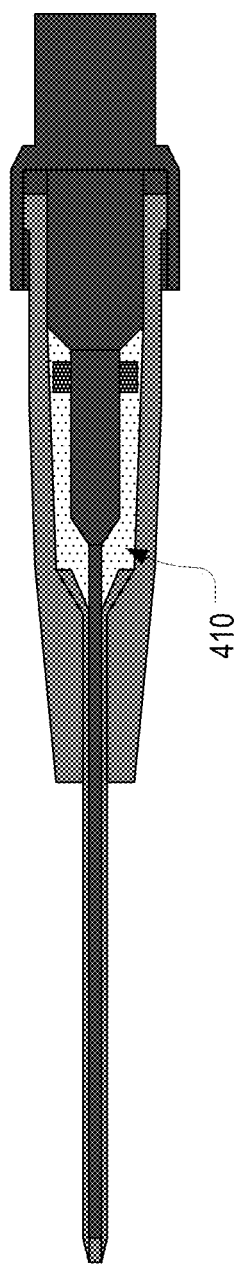

FIGS. 4A and 4B provide an example of how an antimicrobial ring 410 on an obturator can disperse antimicrobial agents into fluid contained within a vascular access device. As with FIG. 3B, FIG. 4B illustrates that antimicrobial agents (represented as white dots) contained within or on the antimicrobial component are dispersed into fluid (represented as black dots) contained within the lumen of the device.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A vascular access system, the vascular access system comprising:
   a vascular access device comprising a catheter extending from a distal end of the vascular access device; and
   an obturator, comprising:
      a catheter portion, wherein when the obturator is secured to the vascular access device, the catheter portion extends through a lumen of the vascular access device and into a proximal end of the catheter of the vascular access device, wherein the catheter portion includes a first outer diameter;
      a middle portion positioned within the lumen of the vascular access device when the obturator is secured to the vascular access device, wherein the middle portion includes a second outer diameter;
      a base portion that seals the lumen when the obturator is secured to the vascular access device, wherein the base portion includes a third outer diameter, wherein the second outer diameter is less than the third outer diameter and greater than the first outer diameter, wherein the base portion is inserted into the lumen of the vascular access device;
      an antimicrobial ring positioned around the middle portion and configured to release an antimicrobial agent, wherein the antimicrobial ring is configured to be positioned within the lumen while the catheter portion is inserted into the catheter, wherein the antimicrobial agent is contained within a material of the antimicrobial ring or on a surface of the material, wherein an inner diameter of the antimicrobial ring is approximately equal to the second outer diameter, wherein an outer diameter of the antimicrobial ring is less than the third outer diameter; and
      a cap portion configured to secure the obturator to the vascular access device.

2. The vascular access system of claim 1, wherein the catheter portion includes an antimicrobial coating, wherein antimicrobial coating comprises a dissolvable coating.

3. The vascular access system of claim 2, wherein the antimicrobial coating comprises a base material matrix that elutes the antimicrobial agent.

4. The vascular access system of claim 3, wherein the base material matrix is cured onto the catheter portion.

5. The vascular access system of claim 2, wherein the antimicrobial coating is contained on a length of the catheter portion that is positioned within the catheter.

6. The vascular access system of claim 5, wherein the length of the catheter portion also extends into the lumen of the vascular access device.

7. The vascular access system of claim 1, wherein the third outer diameter is substantially the same as the diameter of the lumen of the vascular access device.

8. An obturator for a vascular access device, the obturator comprising:
   a catheter portion configured to be inserted through a lumen of the vascular access device and into a proximal end of a catheter of the vascular access device while the catheter is placed intravenously within a patient, wherein the catheter portion includes a first outer diameter, wherein the catheter portion further includes an antimicrobial component configured to release an antimicrobial agent into fluid contained within the vascular access device;
   a middle portion configured to be positioned within the lumen of the vascular access device while the catheter portion is inserted into the catheter, wherein the middle portion includes a second outer diameter that is constant along at least a portion of the middle portion, wherein a distal end of the middle portion proximate the catheter portion is tapered;
   a base portion that seals the lumen when the obturator is secured to the vascular access device, wherein the base portion includes a third outer diameter, wherein the second outer diameter is less than the third outer diameter and greater than the first outer diameter, wherein the base portion is inserted into the lumen of the vascular access device, wherein the base portion is inserted into the lumen of the vascular access device, wherein a distal end of the base portion proximate the middle portion is tapered;

a cap portion proximal to the base portion and configured to secure the obturator to the vascular access device;

a ring positioned around the middle portion, wherein the ring is configured to be positioned within the lumen while the catheter portion is inserted into the catheter; and an antimicrobial coating disposed on a surface of the ring.

9. The obturator of claim 8, wherein the ring comprises a base material matrix that elutes the antimicrobial agent.

10. The obturator of claim 9, wherein the base material matrix forms the antimicrobial coating on the surface of the ring.

11. The obturator of claim 8, wherein the antimicrobial component includes an antimicrobial coating configured to release the antimicrobial agent into the fluid contained within the vascular access device.

12. The obturator of claim 11, wherein the antimicrobial coating is dissolvable.

13. The obturator of claim 11, wherein the antimicrobial coating comprises a base material matrix that elutes the antimicrobial agent.

14. The obturator of claim 8, further comprising:
a base portion having a diameter substantially the same as the diameter of the lumen, the base portion configured to seal the lumen when the obturator is secured to the vascular access device.

* * * * *